United States Patent [19]

Ozaki et al.

[11] Patent Number: 5,231,651
[45] Date of Patent: Jul. 27, 1993

[54] X-RAY COMPUTERIZED TOMOGRAPHIC METHOD AND APPARATUS WITH SIMPLE PROGRAMMABLE ANATOMICAL SELECTING OPERATION

[75] Inventors: Masahiro Ozaki, Ootawara; Hisahiro Shinohara, Yaita, both of Japan

[73] Assignee: Kabushiki Kaisha Toshiba, Kanagawa, Japan

[21] Appl. No.: 865,666

[22] Filed: Apr. 7, 1992

Related U.S. Application Data

[63] Continuation of Ser. No. 678,371, Apr. 1, 1991, abandoned.

[30] Foreign Application Priority Data

Mar. 30, 1990 [JP] Japan ................................ 2-085173

[51] Int. Cl.$^5$ ................................................ A61B 6/00
[52] U.S. Cl. ........................................ 378/4; 378/91; 378/95; 378/99; 378/205; 378/901
[58] Field of Search ....................... 378/4, 901, 62, 99, 378/91, 95, 8, 205

[56] References Cited

U.S. PATENT DOCUMENTS

4,773,086  9/1988  Fujita et al. ............................ 378/4
5,018,178  5/1991  Katsumata ............................ 378/91

Primary Examiner—Paul M. Dzierzynski
Assistant Examiner—Kim-Kwok Chu
Attorney, Agent, or Firm—Finnegan, Henderson, Farabow, Garrett & Dunner

[57] ABSTRACT

In an X-ray CT (computerized tomographic) apparatus, a simple programmable anatomical selecting operation is realized. The X-ray CT apparatus comprises: selecting means for selecting at least one of imaging sorts and imaging portions with respect to a biological body under medical examination; means for programming a medical examination scheme based upon the one of imaging sorts and imaging portions of the biological body; first storage means for storing therein the programmed examination scheme; and, means for reading out the programmed examination scheme from the first storage means so as to sequentially execute functions of the programmed examination scheme.

10 Claims, 10 Drawing Sheets

INSPECTION SCHEME 50

| STEP | ITEMS | FUNCTIONS | SETTING |
|---|---|---|---|
| STEP 10 | VOICE | MAKE VOICE | SET SORT OF VOICE, e.g., "COMMENCE INSPECTION" |
| STEP 11 | SCANNOGRAM | ACQUIRE SCANNOGRAM | SET IMAGING CONDITIONS |
| STEP 12 | SCANNO-SCHEME | DETERMINE SCANNING POSITIONS ON SCANNO-GRAM | NO SETTING |
| STEP 13 | COUCH POSITION SETTING | CHANGE DISPLAY VALUE OF COUCH POSITION | SET DISPLAY VALUE |
| STEP 14 | SCANNING | PERFORM SCANNING OPERATION UNDER SET CONDITIONS | SET SCANNING CONDITIONS (SEE FIG.6) |
| STEP 15 | ADDITIONAL SCANNING | ADDITIONALLY PERFORM SCANNING OPERATION UNDER SAME CONDITION AS THAT OF JUST BEFORE SCANNING, OR UNDER PARTIALLY CHANGED CONDITION | NO SETTING |

FIG.3C

| STEP | ITEMS | FUNCTIONS | SETTING |
|---|---|---|---|
| STEP 16 | CONTRAST MEDIUM SETTING | PERFORM AGAIN SCANNING OPERATION UNDER SAME SET CONDITIONS AS STEPS 14 AND 15 AT SAME POSITION (SEE FIG.7) | NO SETTING |
| STEP 17 | IMAGE DATA TRANSFER | TRANSFER IMAGE DATA ACQUIRED DURING PRESENT EXAMINATION TO EXTERNAL STORAGE MEDIUM | SET EXTERNAL STORAGE MEDIUM (DESTINATION) |
| STEP 18 | AUTO X-RAY FILM PHOTOGRAPHY | AUTOMATICALLY PHOTOGRAPH ACQUIRED IMAGE DATA BY X-RAY FILM OF MULTIFORMAT CAMERA | SET PHOTOGRAPHING CONDITIONS, e.g., CONTRAST BY MULTIFORMAT CAMERA |
| STEP 19 | VOICE | MAKE VOICE | |

| CONVENTIONAL CT SYSTEM | INVENTIVE CT SYSTEM |
|---|---|
|  | (INITIATION)<br>TOUCH "SCHEME 50" &<br>DEPRESS "STARTING" SWITCH 3A |
| WHILE DEPRESSING SWITCH OF INTERPHONE, OPERATOR SAYS "START EXAMINATION" | SYNTHESIZED VOICE "START EXAMINATION" IS PRODUCED |
| SELECT X-RAY CONDITION BY DEPRESSING SELECTION BUTTON AND DEPRESS START BUTTON | DEPRESS "STARTING" SWITCH |
| DETERMINE SLICE POSITIONS | DETERMINE SLICE POSITIONS |
| INPUT DISPLAY VALUE OF COUCH POSITION | DISPLAY VALUE IS AUTOMATICALLY SET |
| DEPRESS SWITCH FOR TRANSPORTING COUCH | DEPRESS SWITCH FOR TRANSPORTING COUCH |

| TUBE CURRENT | SLICE WIDTH | PITCH | FUNCTION | REPETITION |
| --- | --- | --- | --- | --- |
| 140 mA | 5 mm | 5 mm | 2 | 1 |
| 110 mA | 5 mm | 5 mm | 2 | 3 |
| 110 mA | 10 mm | 10 mm | 2 | 8 |

FIG.7

DETAILED FUNCTIONS FOR SETTING CONTRAST MEDIUM

① PERFORM SCANNING OPERATION AT THE SAME POSITION AND AT THE SAME CONDITIONS AS PREVIOUS STEPS 14 AND 15.

② CHECK WHETHER OR NOT SAME SCANNING POSITION DURING ADDITIONAL SCANNING. IF YES, THEN WARNING IS MADE.

③ ELIMINATE SAME SCANNING POSITION DURING ADDITIONAL SCANNING AND EXECUTE FURTHER SCANNING.

④ EXECUTE SCANNING IN OPPOSITE SEQUENCE.

FIG.8

MEMORY 8

SCANNING CONDITION SETTING TABLE 80

| 140 mA | 5 mm | 5 mm | 5 mm | 1 mm | ---- |
| 110 mA | 5 mm | 5 mm | 5 mm | 3 mm | ---- |
| 110 mA | 10 mm | 10 mm | 10 mm | 8 mm | ---- |

CONTRAST MEDIUM SETTING TABLE 82

| 140 mA | 5 mm | 5 mm | 5 mm | 1 mm | ---- |
| 110 mA | 5 mm | 5 mm | 5 mm | 3 mm | ---- |
| 110 mA | 10 mm | 10 mm | 10 mm | 4 mm | ---- |
| 80 mA | 10 mm | 10 mm | 10 mm | 4 mm |  |

X-RAY COMPUTERIZED TOMOGRAPHIC METHOD AND APPARATUS WITH SIMPLE PROGRAMMABLE ANATOMICAL SELECTING OPERATION

This application is a continuation of application Ser. No. 07/678,371, filed Apr. 1. 1991, now abandoned.

BACKGROUND OF THE INVENTION

1. Field of the Invention

The present invention relates to an X-ray CT (computerized tomographic) method and apparatus capable of performing a desirable routine inspection based on a preset examination plan.

2. Description of the Related Art

In general, X-ray CT apparatuses are equipped with a PAS (programmable anatomical selection) function. This PAS function implies that scanning conditions are previously programmed in accordance with imaging purposes or modes and imaging portions of biological bodies under medical examination, and the resultant scanning conditions may be set to storage devices by operating the relevant operation buttons (keys) of the keyboard, or panel. In accordance with the conventional CT apparatus with such a PAS function, since only one scanning condition is set by a single key operation, there is such a problem that when a routine inspection or examination is carried out, the various key operations required for this routine inspection or examination must be repeated. Also, there is another problem that these key operations merely enable such scanning conditions concerning the practical medical data acquisition to be set.

Figure 1:
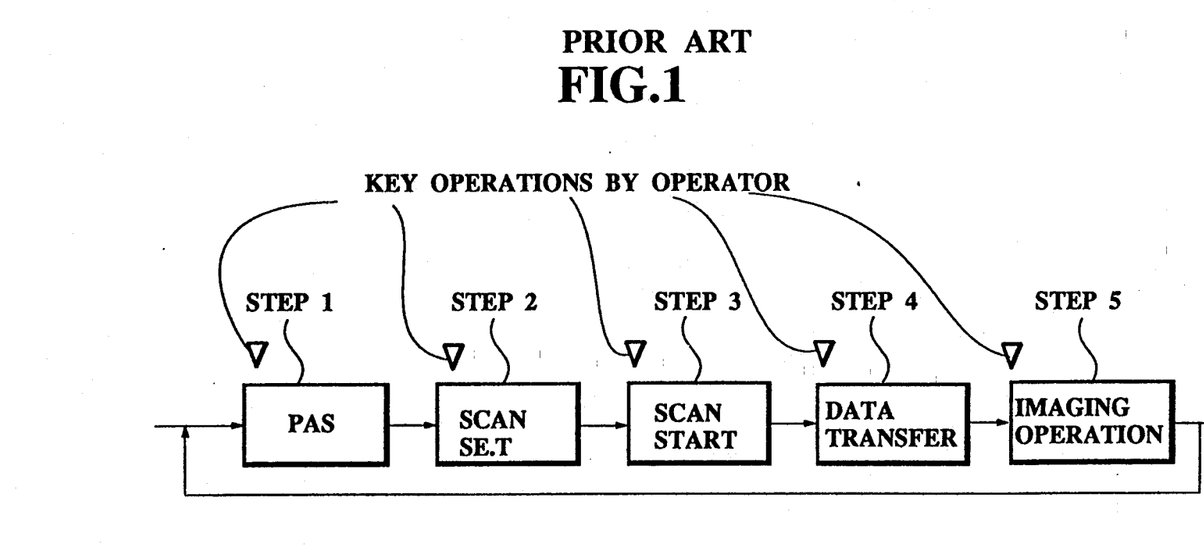
FIG. 1 is a schematic block diagram for explaining the routine examination of the conventional X-ray apparatus.

In FIG. 1, there is shown an inspection or examination example with employment of the conventional X-ray CT apparatus, in which the following execution processes for X-ray CT imaging operation are represented: that is, at a first step 1, after the scanning condition has been set to "PAS", the scanning operation is prepared at a second step 2. Then, the scanning operation is commenced to acquire CT images of a biological body under medical examination at a step 3. Subsequently, after the CT images are transferred to the optical disk (not shown) so as to be filed therein at a step 4, the CT images are photographed by a multiformat camera (not shown) at a step 5. As previously described, the manual operations by the operator are necessarily required at the respective steps in order to complete a series of medical examination. Moreover, when medical examinations similar to the above-described examination are repeated, such manual operations (key or button manipulations) are further required.

As stated above, since only single scanning condition can be set by operating the button or key one time in the conventional X-ray CT apparatuses, there is a problem that a large quantity of key operations must be executed by the operator when the routine inspection or examination for CT imaging is carried out. Furthermore, there is a limitation that operations related to only actual image acquisitions may be set. In other words, such a heavy and cumbersome key or button operation must be loaded by the operator while executing the medical routine examination on the X-ray CT imaging apparatus. Also, such a key operation has a limited instruction or function.

SUMMARY OF THE INVENTION

The present invention has been made in an attempt to solve the above-described various problems, and therefore has an object to provide an X-ray CT apparatus capable of executing a medical routine examination by manipulating a key or button only one time.

The X-ray CT apparatus, according to the present invention, comprises:

selecting means (2:3) for selecting at least one of imaging modes and imaging portions with respect to a biological body (18) under medical examination;

means (6:7) for programming a medical examination scheme (50) based upon said one of imaging modes and imaging portions of the biological body (18);

first storage means (11) for storing therein said programmed examination scheme (50); and, means (7:12:13:15:16) for reading out the programmed examination scheme (50) from said first storage means (11) so as to sequentially execute functions of the programmed examination scheme (50).

BRIEF DESCRIPTION OF THE DRAWINGS

For a better understanding of the present invention, reference is made to the following descriptions to be read in conjunction with the accompanying drawings, in which.

DETAILED DESCRIPTION OF THE PREFERRED EMBODIMENTS ENTIRE SYSTEM

Figure 2:
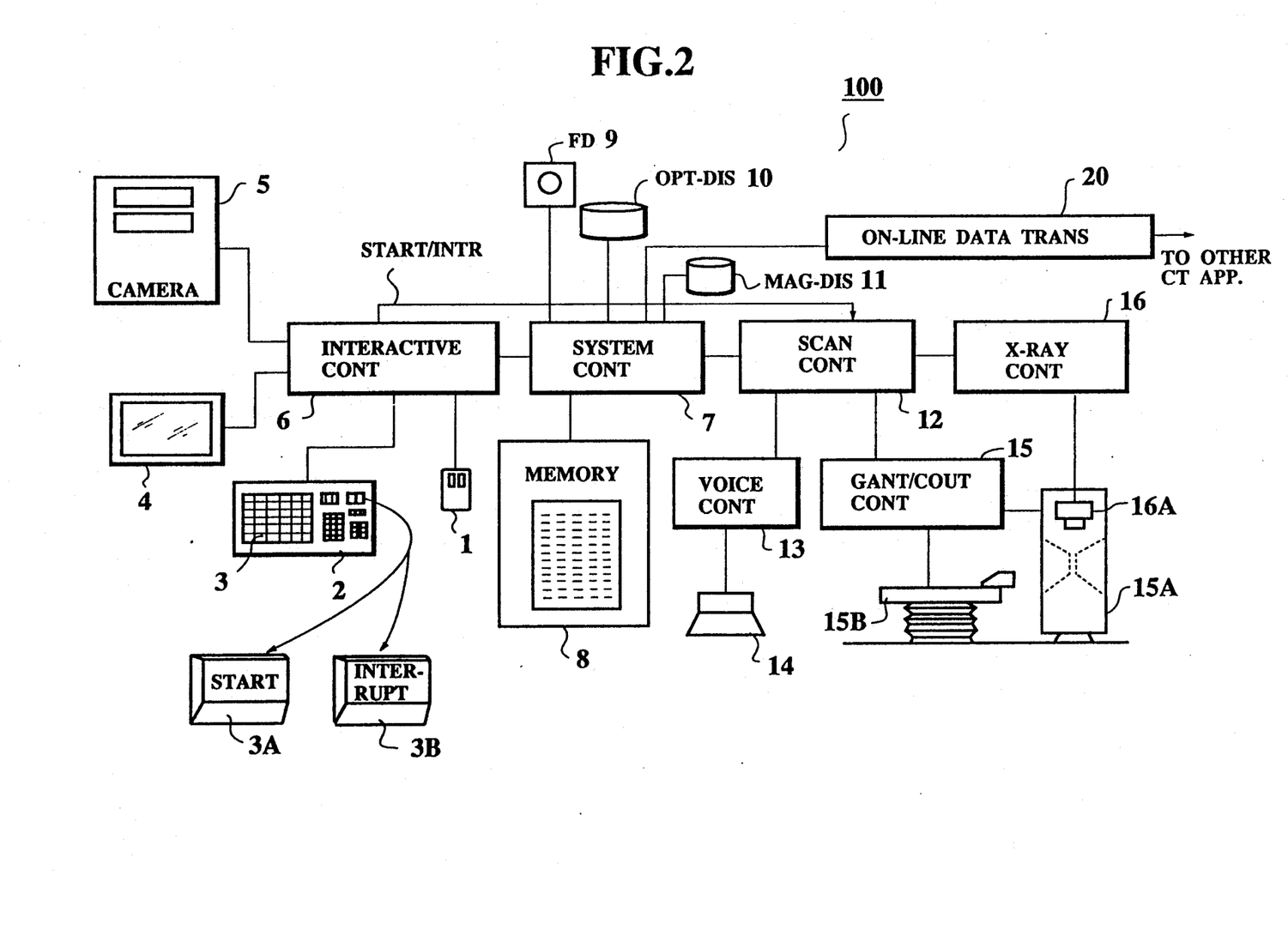
FIG. 2 is a schematic block diagram for representing an entire system of an X-ray CT apparatus according to a first preferred embodiment of the present invention.

Referring now to FIG. 2, an entire system arrangement of an X-ray CT apparatus 100 according to a first preferred embodiment of the present invention.

In FIG. 2, a mouse 1, a keyboard 2 and a display screen 3 with a touch sensor are provided as an input means. Both a starting switch "3A" and an interrupt switch "3B" are also provided as the input means. A monitor 4 and a multiformat camera 5 are employed. An interactive control unit 6 is connected to all of the above-described devices 1 through 5. A memory 8, a floppy disk 9, an optical disk 10, and a magnetic disk 11 are employed as a data storage means. Furthermore, a scanning control unit 12 is employed to control a gantry/couch control unit 15 and an X-ray control unit 16. The gantry/couch control unit 15 controls a gantry 15A and a couch 15B on which a biological body under medical examination (not shown in detail) is mounted, whereas the X-ray control unit 16 controls an X-ray tube 16A in such a manner that X-ray projections emitted from an X-ray tube 16A are controlled by the X-ray control unit 16 in conjunction with the controls of the gantry/couch control unit 15. As a result, the desired X-ray scanning control is performed under control of the scanning control unit 12 (will be discussed later). A speaker 14 and a voice control unit 13 are connected to the scanning control unit 12. An entire system of the X-ray CT apparatus 100 shown in FIG. 2 is controlled by a system control unit 7. Furthermore, an on-line data transfer unit 20 is coupled to the system control unit 7 so as to transfer data on CT images to other CT apparatuses (not shown n detail).

Overall Scheme Execution

Referring back to the system arrangement of the first X-ray CT apparatus 100 shown in FIG. 2, an overall scheme execution will now be summarized.

In FIG. 2, when an operator touches a preselected position of the display screen 3 with touch sensors, this touched position is recognized by the interactive control unit 6 and then the touched positional data is transferred from this control unit 6 to the system control unit 7. The system control unit 7 reads out the medical examination scheme data corresponding to the touched positional information from the magnetic disk 11, and sends the read scheme data to the memory 8.

Subsequently, the functions are successively read out from the examination scheme in the memory 8 under control of the system control unit 7 and then are transferred to the scanning control unit 12. The scanning control unit 12 interprets the various functions from the system control unit 7 and also transfers necessary instructions to the X-ray control unit 16, gantry/couch control unit 15, and voice control unit 13. Upon reception of these instructions, the respective control units 13, 14 and 15 execute these instructions. When these control operations are effective in conjunction therewith, the scanning control unit 12 sends instructions to the relevant control units. For the sake of safety, an instruction by an operation will be given in the following flow operations: a commencement by the keyboard 2; the interactive control unit 6; the scanning control unit 12; and the respective control units 13, 15, 16.

Until the last function of this examination scheme is completed, the operations after sequential function-reading operation are repeatedly executed.

First Medical Examination By X-ray CT Apparatus 100

Figure 3A:
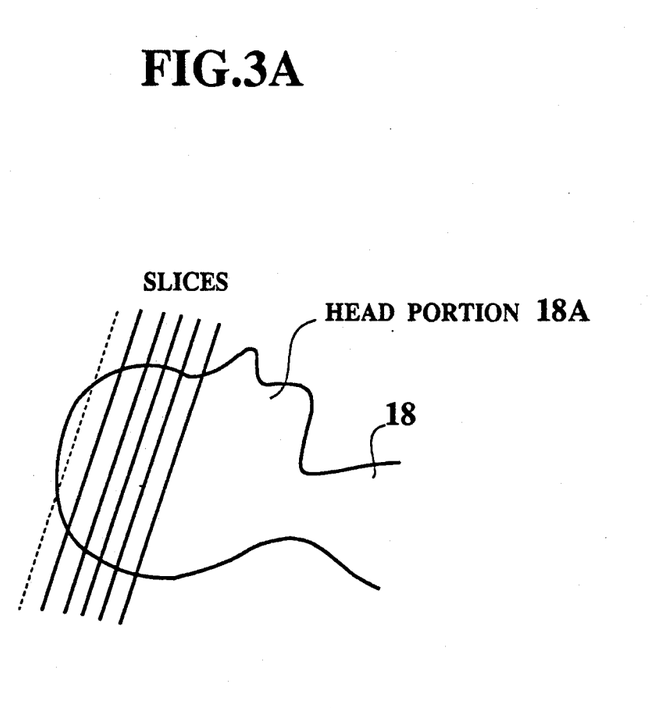
FIG. 3A, 3B and 3C represent an examination or inspection scheme 50 and slice positions.
Figure 3B:
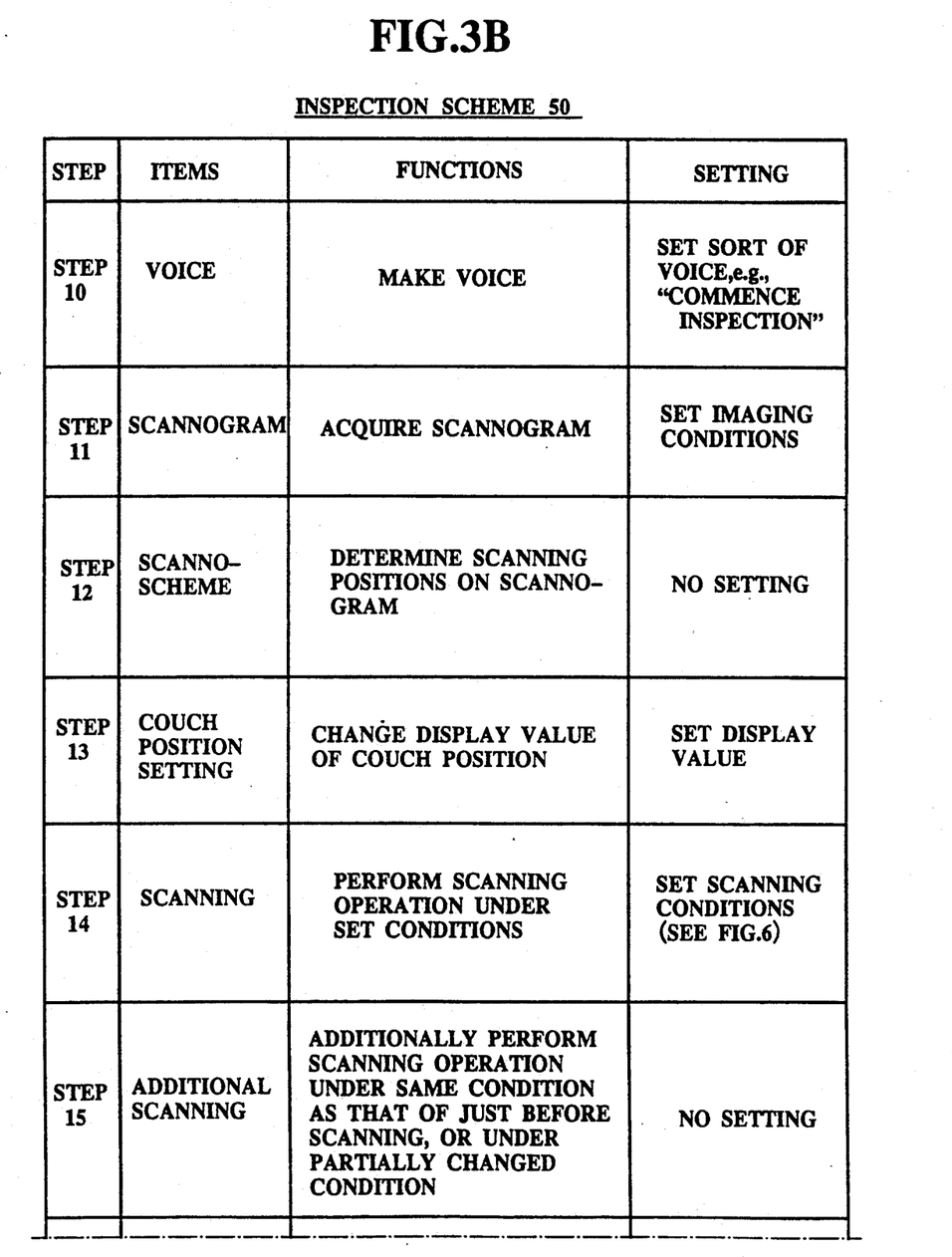
Figure 3C:
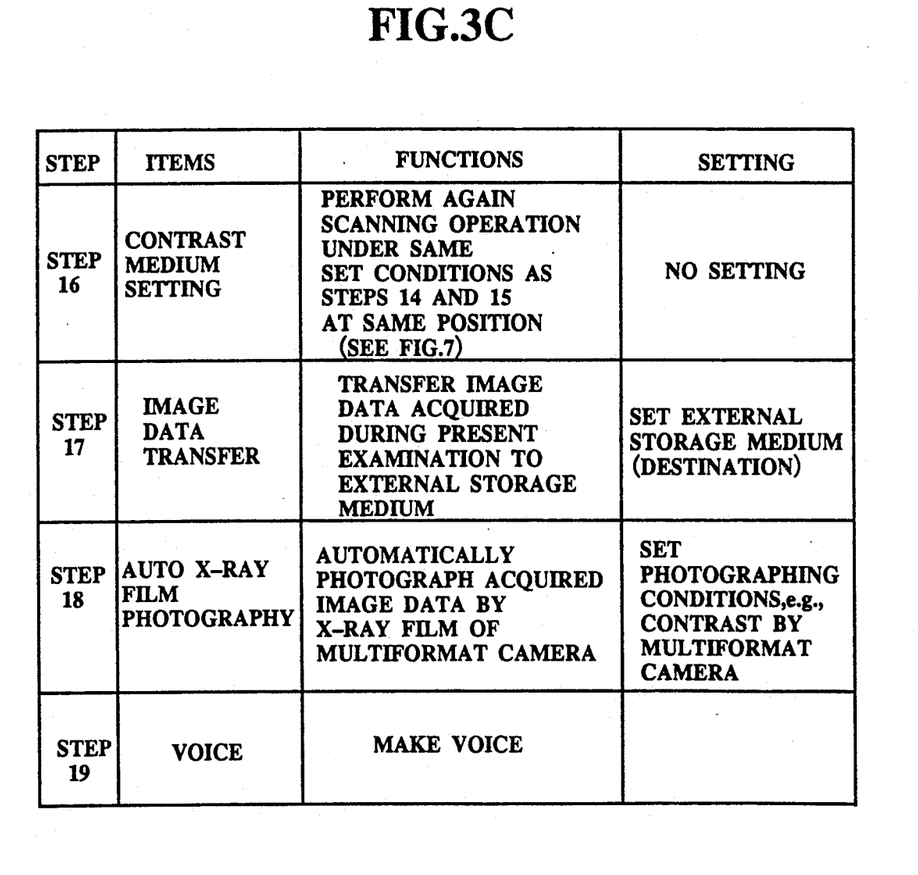

A first medical examination executed by the X-ray CT apparatus 100 will now be described with reference to FIGS. 2 and 3. FIG. 3A represents a relationship between slice positions and a head portion 18A of a biological body 18 under medical examination. FIG. 3B and 3C is a list for explaining an overall step of examination or inspection scheme 50 with respect to the head portion 18A of the biological body 18.

Generally speaking, a medical inspection or examination carried out by an X-ray CT apparatus is performed by combining various functions in order to be adapted to an imaging purpose and an imaging portion of a biological body under medical examination. As previously explained, since the most of these functions are operated independently of other functions, an operator must execute each of these functions so as to be adapted to its inspection purpose in the conventional X-ray CT apparatuses.

To the contrary, a first medical examination accuracy to a first preferred embodiment of the present invention may be realized by executing only simple operation processes as follows.

In the X-ray CT apparatus 100 shown in FIG. 2, interaction is performed by employment of the input/output means such as the monitor 4, keyboard 2 and mouse 1, an examination scheme suitable for an imaging purpose and an imaging portion, i.e., the head portion 18A of the biological body 18, is produced and then is stored in the external storage medium, i.e., the magnetic disk unit 11. This examination scheme is constructed of a flow of functions and conditions set to the respective functions, as illustrated in FIG. 3B and 3C. The function described in this scheme 50 corresponds to a single operation or execution in the medical examinations with employment of the X-ray CT apparatus 100, but may not correspond thereto, depending upon performances of the respective CT apparatuses. For instance, in a continuously rotatable X-ray CT apparatus, a scanning operation does not correspond to only one scanning operation, but may be distinguishable from each other, e.g., a single scanning operation and a continuous scanning operation.

Next, to utilize this scheme, several tens of schemes as represented in FIG. 3B and 3C must be previously formed to be adapted to the imaging purposes and also imaging portions. In general, it is known that 30 to 50 modes of inspection schemes for the X-ray CT inspection including also the specific inspection must be previously prepared. It should be understood that when several tens of different inspection schemes have been once formed, an operator merely makes a selection among several tens of different inspection schemes, depending upon an instruction by a doctor.

As a consequence, according to the first X-ray CT apparatus 100 of the invention, the display screen 3 with the touch sensor shown in FIG. 2 is employed so as to realize an easy scheme selection. In this scheme selection, there are provided on the display screen 3 first schemes with higher selecting degrees irrelevant to diagnostic portions and also second schemes in which diagnostic portions have been grouped, as illustrated in FIG. 4.

Figure 4:
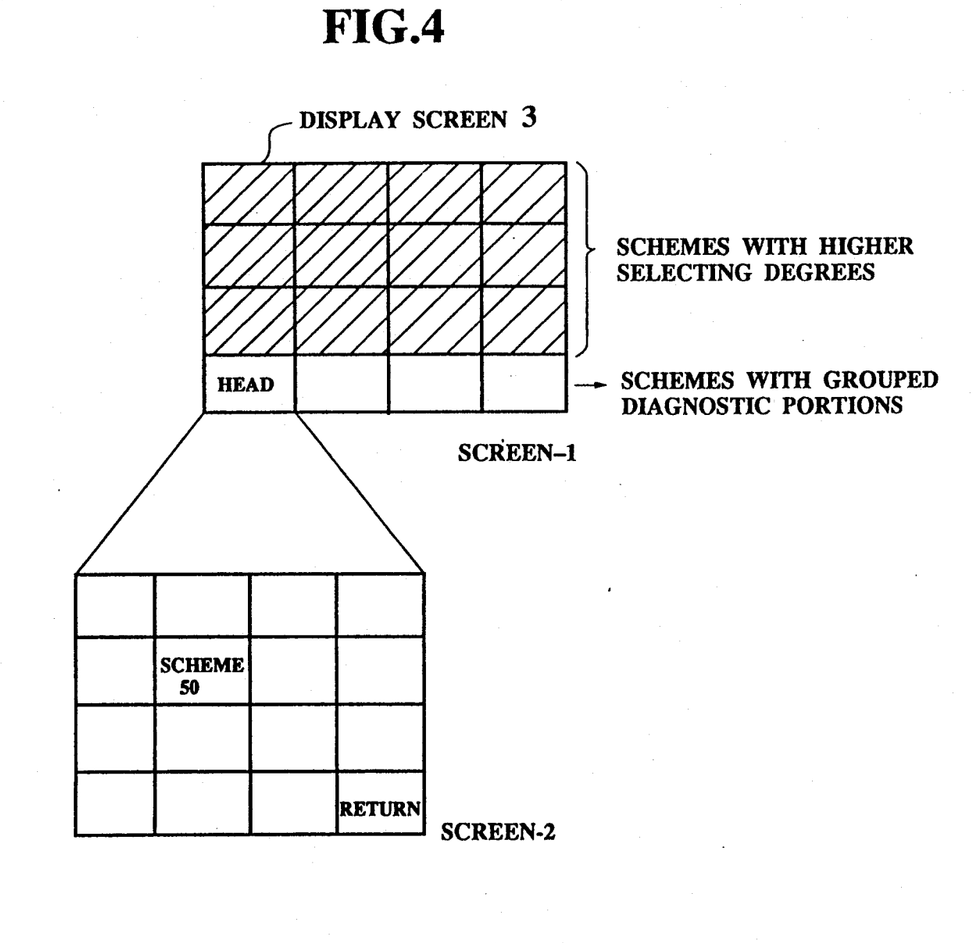
FIG. 4 pictorically represents screen information of the display screen 3 with touch sensor.

In FIG. 4, when an operator touches an indication "HEAD" in a screen-1, the touch sensor is brought into an active state, so that a screen-2 is displayed on the display screen 3. After completion of the scheme selection, the operator touches an indication "RETURN" and thus the screen-1 is again displayed.

Furthermore, these inspection schemes may be freely rearranged in such a manner that any operations can readily use these inspection schemes, or easily memorize the titles of the inspection schemes. It should be noted that since the above-described examination scheme 50 shown in FIG. 3B and 3C has not so higher selecting degrees, this scheme 50 is arranged in the group named "head".

Figure 5:
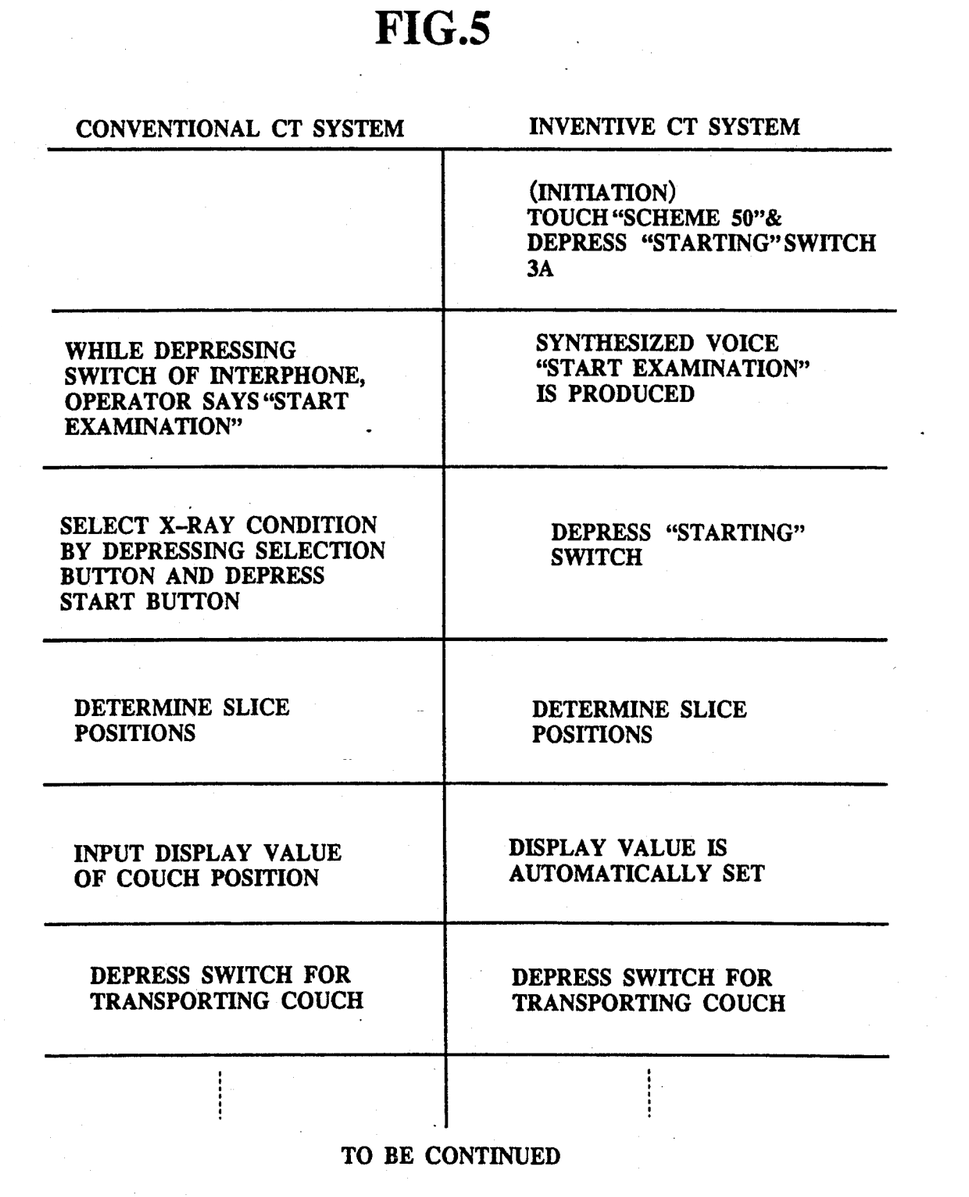
FIG. 5 is a comparison list between the conventional CT system and inventive CT system.

For a better understanding of various merits of the above-described first medical examination (i.e., scheme 50), a reference is made of a comparison list shown in FIG. 5.

As apparent from the comparison list, even if the contents or the respective functions defined in the conventional CT system are the same as those of the inventive CT system, the operator must consider the operation of the subsequent step in the conventional CT system. To the contrary, the desired medical inspection may be automatically executed in accordance with the preselected inspection scheme in the X-ray CT system of the present invention.

Interruption Of Setting Scanning Conditions

Figure 6:
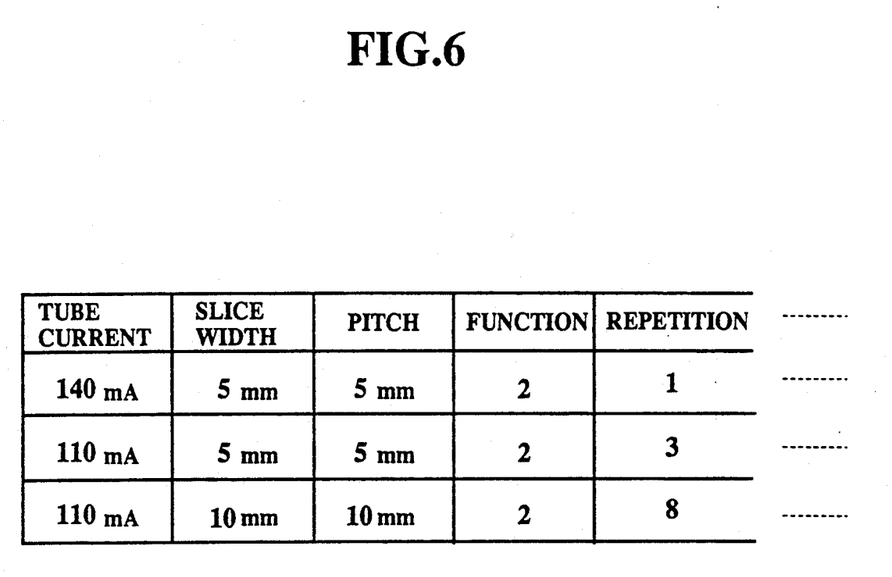
FIG. 6 represents contents of scanning conditions.

Referring back to the step 14 (setting of scanning conditions) of the inspection scheme 50 shown in FIG. 3B, the contents of the scanning conditions will now be described more in detail. FIG. 6 represents multiple scanning conditions to be set at the step 14.

Then, according to the first medical examination, the execution of the step 14 may be interrupted and the scanning condition (see FIG. 6) which have been preset may be varied by an operator.

Such an interruption is carried out as follows. In the system shown in FIG. 2, when an operator depresses the "interrupt" switch 3B employed in the keyboard 2, the interrupt instruction is supplied via the interactive control unit 6, scanning control unit 12 and system control unit 7 to the relevant control units 12, 13, 15 and 16, whereby the presently executed process is interrupted. The system control unit 7 automatically receives the interrupt instruction to perform an interactive operation for an interactive operation for producing another inspection scheme. In case that the inspection scheme is temporarily changed, the contents of this inspection scheme on the memory 8 are rewritten. In case that the inspection scheme is entirely changed, the contents of this inspection scheme stored in the magnetic disk unit 11 are rewritten. Thereafter, the starting switch 3A is depressed so as to restart the inspection scheme.

Input Source Selection

Furthermore, according to the first medical inspection scheme, the inspection scheme previously stored in the magnetic disk unit 11 may be widely utilized. For instance, if the excellent inspection scheme could be established, this scheme may be similarly utilized in other X-ray CT apparatuses (not shown in detail) via the on-line data transfer unit 20 shown in FIG. 2. Furthermore, both a floppy disk unit 9 and an optical disk unit 10 are employed as an auxiliary storage unit.

Second Medical Inspection Scheme

In the conventional X-ray system, only conditions required for one scanning operation are stored and utilized. However, in a medical examination with an X-ray CT system, a plurality of conditions (e.g., tube currents, slice widths and pitches) are combined with each other in view of improving efficiencies and image qualities, and also of reducing X-ray exposure amounts. Therefore, an operator must change these conditions for every scanning operation in the conventional CT system.

To the contrary, various conditions for a plurality of scanning operations may be previously stored and utilized according to the second preferred embodiment.

In the X-ray CT system 100 shown in FIG. 2, when the scanning step 14 becomes effective, the system control unit 7 supplies one sort of scanning condition to the scanning control unit 12. This scanning condition is selected from the contents shown in FIG. 6. In response to this scanning condition, the scanning control unit 12 supplies the control conditions to the relevant control units 13, 15, 16. As a result, each of these control units 13, 15, and 16 execute the relevant instructions. Subsequently, a series of the above-described operations is repeated until all of the conditions as listed in FIG. 6 are completed.

There is a similar advantage to that of the above-described second medical examination that all of the scanning conditions are supplied at one time to the scanning control unit 12 and are successively processed. There is another particular advantage that since a plurality of scanning conditions may be previously stored and utilized, cumbersome operation may be avoided and also erroneous changes in the scanning conditions may be avoided.

Third Medical Examination Scheme

Figure 7:
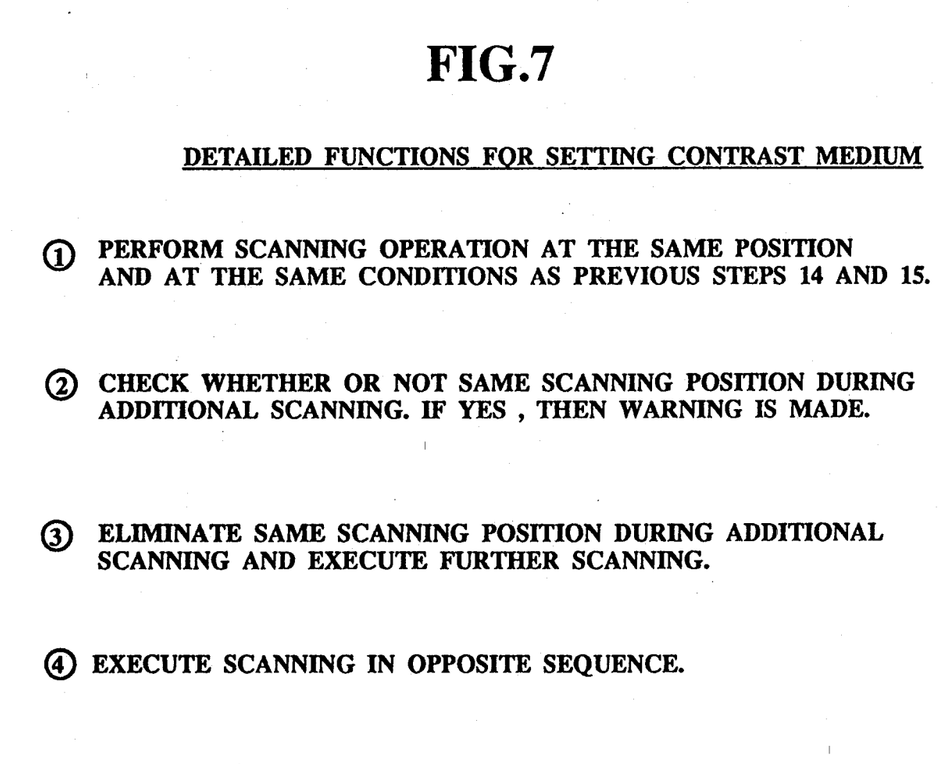
FIG. 7 represents detailed functions for setting a contrast medium.

FIG. 7 shows a detailed function of the contrast medium setting step 16 represented in FIG. 3C.

Generally speaking, an X-ray examination with employment of an X-ray contrast medium is executed in combination with a normal X-ray examination without using the X-ray contrast medium, since a diseased portion of a biological body may be discovered by comparing the same diagnostic portion thereof imaged under the normal examination and contrast medium examination. As a consequence, the X-ray examination with the X-ray contrast medium is carried out under the same scanning conditions and at the same diagnostic portion of the biological body as those of the normal X-ray examination. As previously described with reference to FIG. 6, a large quantity of scanning conditions (e.g., tube currents, slice widths, pitches, and scanning repetition) must be set so as to realize the above-described X-ray contrast examination.

In accordance with a third medical inspection or examination scheme according to the present invention, such an X-ray contrast examination may be achieved with very simple operation. To this end, the following process is performed (see FIG. 8).

Figure 8:
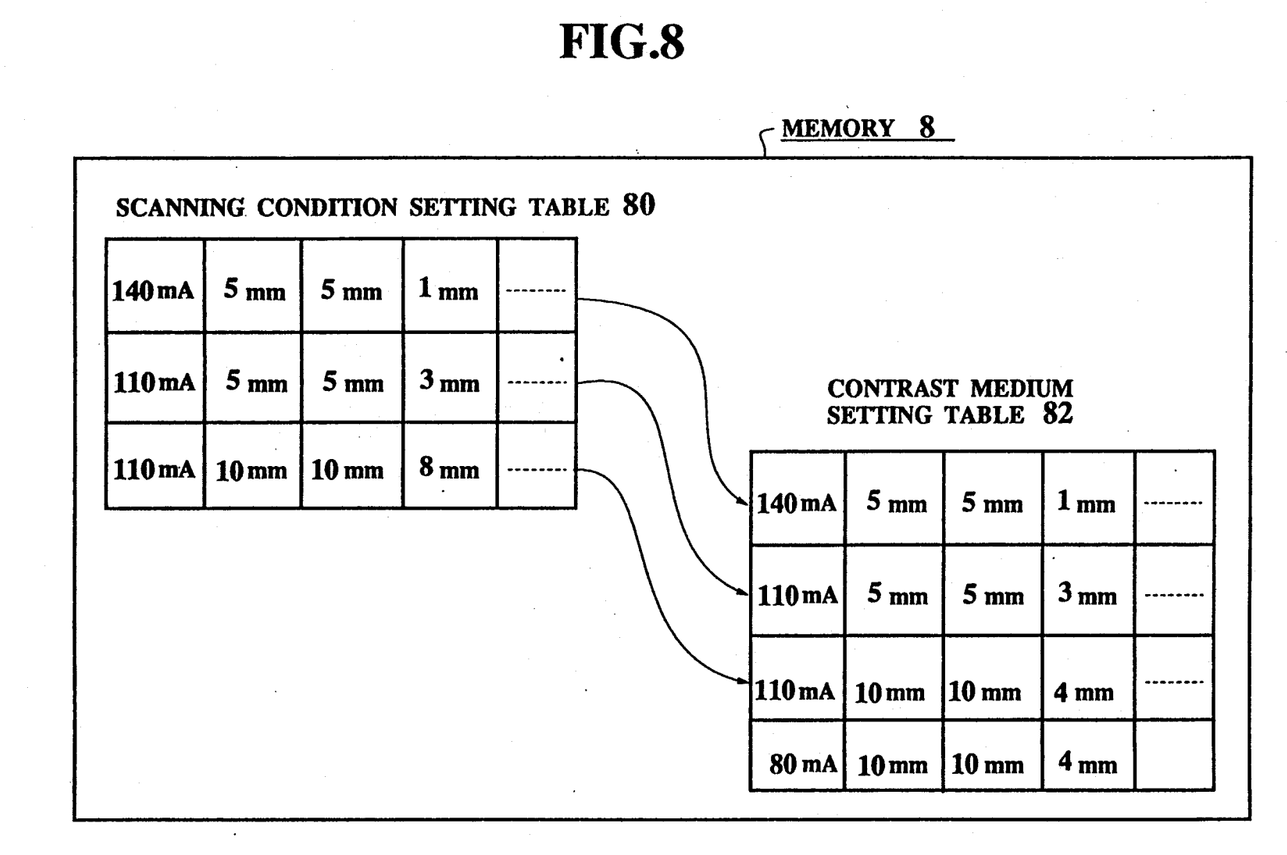
FIG. 8 pictorically shows setting tables of the memory 8.

As seen from FIG. 8, the scanning conditions which were executed at the step 14 of FIG. 3B have been written into a scanning condition setting table 80 of the memory 8. After the scanning operation under the above-described scanning conditions is completed, the data on these scanning conditions are transferred from the scanning control unit 12 to a contrast medium setting table 82 of the memory 8 so as to be written in this table 82. As a consequence, even when the scanning operation is interrupted and the scanning conditions are changed, the necessary scanning conditions can be maintained.

Since the memory 8 newly owns the above-described contrast medium setting table 82, the following advantages may be achieved.

That is to say, as precisely described in the detailed functions for setting a contrast medium represented in FIG. 7, it is very common to restart the scanning operation when a biological body moves during the scanning operation. At this time, if the X-ray contrast medium examination is carried out the same diagnostic portion or position of the moved biological body is scanned several times. Such a plurality of scanning operations give unwanted X-ray exposure to the biological body. However, on the other hand, there are possibilities that the same diagnostic portion is scanned several times with a predetermined time interval.

To satisfy the above-explained trade-off conditions, the contrast medium setting functions 2 and 3 shown in FIG. 7 are necessarily required for an X-ray examination with a contrast medium. According to the third medical examination scheme, such functions may be automatically set and executed.

Furthermore, a scanning direction during a normal X-ray examination is substantially fixed. For instance, the normal scanning is carried out front a head portion of a patient to a leg portion thereof during an abdomen examination. However, during an X-ray contrast medium examination, a scanning direction is always not limited to only one direction, because flow directions of the X-ray contrast medium injected into the patient give important aspect. As a consequence, the contrast medium setting function 4 shown in FIG. 7 may satisfy the above-described scan-direction setting operations. According to the third inspection scheme, such a setting operation may be automatically realized.

What is claimed is:

1. An X-ray CT (computerized tomographic) apparatus comprising:
    selecting means for selecting at least one of imaging modes, imaging positions of a biological body under medical examination, and scanning conditions;
    means for programming a medical examination scheme including a plurality of functions for sequential execution based upon said at least one of imaging modes, imaging positions and scanning conditions;
    first storage means for storing therein said programmed examination scheme including the plurality of functions;
    means for manually selecting in a single manipulation a starting instruction; and
    means for reading out the programmed examination scheme from said first storage means in response to the single starting instruction, to sequentially execute the plurality of functions of the programmed examination scheme.

2. An X-ray CT apparatus as claimed in claim 1, further comprising:
    means for interrupting the execution of said programmed examination scheme so as to change the functions thereof.

3. An X-ray CT apparatus as claimed in claim 2, wherein said change in the functions of the programmed examination scheme is temporarily carried out.

4. An X-ray CT apparatus as claimed in claim 2, wherein said change in the functions of the programmed examination scheme is fixedly performed.

5. An X-ray CT apparatus as claimed in claim 1 further comprising:
    second storage means for temporarily storing said programmed examination scheme; and,
    data transfer means for transferring said programmed examination scheme from said first storage means to an external CT system and vice versa.

6. An X-ray CT apparatus as claimed in claim 1, further comprising:
    a multiformat camera for photographing images of the biological body, while executing the functions of the programmed examination scheme by the reading means.

7. An X-ray CT apparatus as claimed in claim 1, further comprising:
    an interactive control unit for controlling the medical examination of the biological body while programming the medical examination by the programming means.

8. An X-ray CT (computerized tomographic) apparatus comprising:
    means for setting a plurality of scanning conditions;
    means for manually selecting in a single manipulation a starting instruction;
    means for selecting said plurality of scanning conditions in accordance with each one of a plurality of slice positions of a biological body under medical examination in response to said single starting instruction; and
    control means for controlling executions of CT operation in response to the selected plurality of scanning conditions.

9. A method for producing a CT (computerized tomographic) image, comprising the steps of:
    selecting at least one of imaging modes, an imaging position of a biological body under medical examination, and scanning conditions;
    programming a medical examination scheme based upon said at least one of imaging modes, imaging position and scanning conditions; and
    sequentially executing functions of said programmed examination scheme in response to a single starting instruction, thereby to obtain said CT image of the biological body.

10. A method as claimed in claim 9, further comprising the steps of:
    setting a plurality of slice positions of a biological body under medical examination;
    sequentially scanning said set plurality of slice positions so as to acquire a plurality of tomographic images;
    injecting an X-ray contrast medium into the biological body after said sequential scanning step; and
    sequentially scanning the said same set plurality of slice positions after injection the X-ray contrast medium into the biological body.

* * * * *

UNITED STATES PATENT AND TRADEMARK OFFICE
CERTIFICATE OF CORRECTION

PATENT NO. : 5,231,651
DATED : July 27, 1993
INVENTOR(S) : Masahiro Ozaki et al.

It is certified that error appears in the above-indentified patent and that said Letters Patent is hereby corrected as shown below:

Claim 10, column 8, line 51, after "injection" insert --of--.

Signed and Sealed this

Twenty-sixth Day of April, 1994

Attest:

BRUCE LEHMAN

*Attesting Officer*     *Commissioner of Patents and Trademarks*